United States Patent [19]

Atwal

[11] Patent Number: 5,006,523
[45] Date of Patent: Apr. 9, 1991

[54] ANTIARRHYTHMIC AGENTS: ARYL CYANOGUANIDINE POTASSIUM CHANNEL BLOCKERS

[75] Inventor: Karnail Atwal, Newtown, Pa.

[73] Assignee: E. R. Squibb & Sons, Inc., Princeton, N.J.

[21] Appl. No.: 427,655

[22] Filed: Oct. 26, 1989

[51] Int. Cl.$^5$ ............... A61K 31/54; A61K 31/495; A61K 31/445; A61K 31/44; A61K 31/415; C07D 401/04; C07D 401/06; C07D 403/10; C07D 233/02; C07D 295/12

[52] U.S. Cl. .................. 514/227.5; 514/212; 514/227.8; 514/231.8; 514/235.5; 514/235.8; 514/237.8; 514/238.2; 514/238.5; 514/252; 514/255; 514/315; 514/317; 514/318; 514/326; 514/331; 514/341; 514/343; 514/401; 514/402; 514/408; 514/422; 514/588; 514/597; 514/602; 514/604; 514/605; 514/609; 514/634; 540/609; 540/610; 544/59; 544/163; 544/360; 544/372; 544/396; 546/191; 546/193; 546/194; 546/223; 546/230; 546/246; 546/278; 548/351; 548/352; 548/566; 548/567; 548/568; 548/569; 564/48; 564/49; 564/50; 564/80; 564/84; 564/90; 564/91; 564/92; 564/99; 564/105

[58] Field of Search .............. 544/59, 360, 163, 372, 544/396; 546/194, 275, 193, 223, 191, 246, 230, 278; 548/352, 351, 566, , 567, 568, 569; 540/609, 610; 564/99, 105, 48, 49, 50, 84, 90, 91, 92, 80; 514/212, 227.5, 238.5, 252, 255, 317, 318, 341, 343, 401, 408, 428, 605, 634, 227.8, 231.8, 235.5, 235.8, 237.8, 238.2, 326, 331, 315, 402, 422, 588, 597, 602, 604, 252, 255, 318

[56] References Cited

U.S. PATENT DOCUMENTS 4,057,636 11/1977 Petersen .................. 546/306
4,876,262 10/1989 Oinuma et al. ............ 546/194
4,895,840 1/1990 Shanklin, Jr. ............. 546/193

FOREIGN PATENT DOCUMENTS 0286277 10/1988 European Pat. Off. .
300908 1/1989 European Pat. Off. .

OTHER PUBLICATIONS

Tilley et al, Chem. Abst. 93-197547h, (1980).
"Pinacidil: A New Antihypertensive Agent", *Drugs Today*, vol. 25, No. 1, pp. 65–74 (1989), I. Ahnfelt-Ronne et al.
"Electrophysioligic and Antiarrhythmic Activities of 4-Amino-N-[2-(diethylamino)ethyl]-3,5-dimethylbenzamide, a Sterically Hindered Procainamide Analogue", *Jour. Med. Chem.*, 1988, vol. 3, No. 7, pp. 1290–1295, D. W. Robertson et al.
"Synthesis and Class III Antiarrhythmic Activity of (Phenylbut-2-enyl)ammonium Salts, Effect of Conformation on Activity", *Jour. Med. Chem.*, 1986, vol. 29, No. 8, pp. 1398–1405, T. K. Morgan et al.
J. R. Harper, Jr., M.D. et al., "A Reexamination of Antiarrhythmic Drug Classification", *CVR&R*, Jun. 1988, pp. 59–65.
R. S. Bexton et al., "Drugs with a Class III Antiarrhythmic Action", *Pharmac. Ther.*, vol. 17, pp. 315 to 355 (1982).
S. Donoghue et al., "Anti-arrhythmic Agents", *Drugs of Today*, vol. 24, No. 1, pp. 39–52, (1988).

Primary Examiner—Cecilia Shen
Attorney, Agent, or Firm—Theodore R. Furman, Jr.

[57] ABSTRACT

Novel compounds of the formula

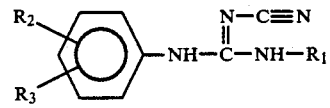

and tautomers thereof are disclosed. These compounds possess potassium channel blocking activity and, as such, are useful as antiarrhythmic agents.

27 Claims, No Drawings

ANTIARRHYTHMIC AGENTS: ARYL CYANOGUANIDINE POTASSIUM CHANNEL BLOCKERS

FIELD OF THE INVENTION

The present invention relates to novel compounds having potassium channel blocking activity which are therefore, useful as antiarrhythmic agents.

BACKGROUND OF THE INVENTION

Petersen, in U.S. Pat. No. 4,057,636, discloses compounds of the formula

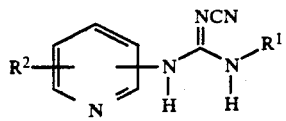

wherein $R^1$ is straight or branched, saturated or unsaturated aliphatic hydrocarbon radical having from 1 to 8 carbon atoms, a cycloalkyl or cycloalkenyl radical having from 3 to 7 carbon atoms, an aryl or an aralkyl radical. These compounds are stated to be useful as antihypertensive agents. It has also been shown that those compounds are antihypertensive agents because of their potassium channel activating properties (I. Ahnfelt-Rønne and H. Jessen Jürgensen, Pinacidil (Pindac ®): A New Antihypertensive Agent in *Drugs of Today*, Vol. 25, No. 1, p. 65–74 (1989)). Further, U.S. Ser. No. 230,209, filed Aug. 9, 1988, entitled "ARYL CYANOGUANIDINES: POTASSIUM CHANNEL ACTIVATORS AND METHOD OF MAKING SAME", discloses compounds of the formula

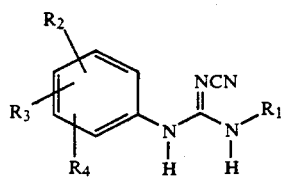

wherein $R_1$ is alkyl, alkenyl, alkynyl, haloalkyl, cycloalkyl, aryl, arylalkyl or cycloalkylalkyl to have potassium channel activating properties.

SUMMARY OF THE INVENTION

In accordance with the present invention novel compounds having potassium channel blocking activity which are therefore useful, for example, as antiarrhythmic agents, are disclosed. These compounds have the general formula

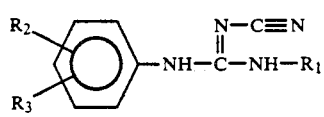

and its possible tautomers

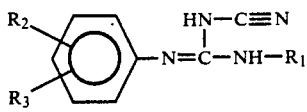

and

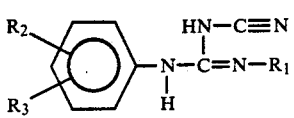

including pharmaceutically acceptable salts wherein $R_1$ is

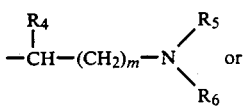

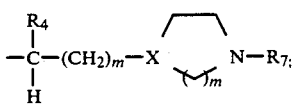

$R_2$ is hydrogen, alkyl, halo, —C≡N,

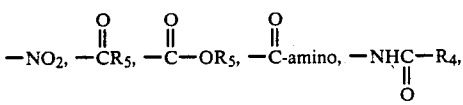

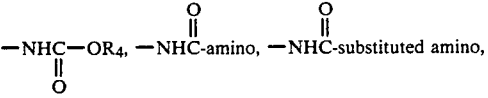

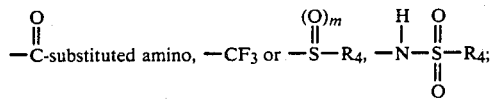

$R_3$ is hydrogen, alkyl, alkenyl, alkynyl, haloalkyl, halo, alkoxy, —NHalkyl, —N—(alkyl)$_2$, —S—alkyl, —O—arylalkyl or —S—arylalkyl;

$R_4$ is hydrogen, alkyl, alkenyl, cycloalkyl, haloalkyl, aryl, arylalkyl, cycloalkylalkyl;

$R_5$ and $R_6$ are $R_4$, together make a 5–7 membered ring which include pyrrolidine, piperidene, morpholine, thiomorpholine, imidazoline, 2-alkylimidazoline, 1-azepinyl;

$R_7$ is $R_4$, diphenylalkyl, pyridyl, pyridylalkyl wherein the pyridyl ring could be substituted with alkyl, arylalkyl, halo, haloalkyl;

m = 1 or 2; and

X is nitrogen or —CH—.

DETAILED DESCRIPTION OF THE PRESENT INVENTION

In accordance with the present invention, it has been found that compounds of formula I, wherein $R_1$ incorporates a basic nitrogen atom, have potassium channel blocking properties and consequently, are useful as antiarrhythmic agents. It is surprising that introduction of a basic nitrogen into $R_1$ changes compounds from having potassium channel activating properties to ones having potassium channel blocking properties.

This invention in its broadest aspects relates to the cyanoguanidine compounds of formula I above, to compositions and the method of using such compounds as cardiovascular agents.

The term lower alkyl used in defining various symbols refers to straight or branched chain saturated hydrocarbon radicals having up to eight carbons, preferably from one to five carbons. Similarly, the terms lower alkoxy and lower alkylthio refer to such lower alkyl groups attached to an oxygen or sulfur.

The term lower alkenyl refers to straight or branched chain hydrocarbon radicals having from two to eight carbons and one double bond, preferably three to five carbons. The term lower alkynyl refers to straight or branched chain hydrocarbon radicals having from two to eight carbons and one triple bond, preferably three to five carbons.

The term cycloalkyl refers to saturated carbocyclic rings of 4 to 7 carbon atoms with cyclopentyl and cyclohexyl being most preferred.

The term halo refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl or mono substituted phenyl, wherein said substituent is lower alkyl of 1 to 4 carbons, lower alkylthio of 1 to 4 carbons, lower alkoxy of 1 to 4 carbons, halo, nitro, cyano, hydroxy, amino, —NH-alkyl wherein alkyl is of 1 to 4 carbons, —N(alkyl)$_2$ wherein alkyl is of 1 to 4 carbons,

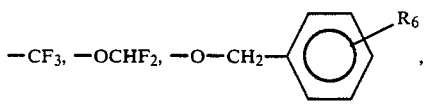

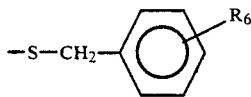

wherein R$_6$ is hydrogen, lower alkyl of 1 to 4 carbons, lower alkoxy of 1 to 4 carbons, lower alkylthio of 1 to 4 carbons, halo, hydroxy or CF$_3$), —O—CH$_2$-cycloalkyl, or —S—CH$_2$-cycloalkyl, and di-substituted phenyl, wherein said substituents are selected from methyl, methoxy, methylthio, halo, CF$_3$, nitro, amino, and OCHF$_2$.

The term "substituted amino" refers to a group of the formula —NZ$_1$Z$_2$ wherein Z$_1$ is hydrogen, alkyl, cycloalkyl, aryl, arylalkyl, cycloalkylalkyl and Z$_2$ is alkyl, cycloalkyl, aryl, arylalkyl, cycloalkylalkyl or Z$_1$ and Z$_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl substituted with alkyl, alkoxy, alkylthio, halo, trifluoromethyl or hydroxy.

To prepare the compounds of formula I, first, an isothiocyanate of the formula

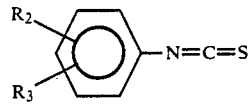

can be reacted with cyanamide of the formula

(wherein M is an alkali metal, e.g., sodium)
in the presence of a solvent, such as ethanol, to provide a compound of the formula

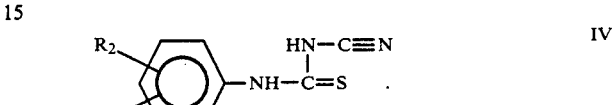

The thiourea of formula IV is thereafter reacted with an alkylating agent, such as dimethyl sulfate or methyl iodide, in the presence of one or more solvents, such as dimethylformamide, tetrahydrofuran or dioxane, to provide a compound of the formula

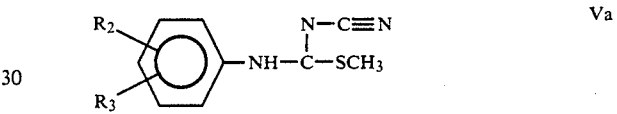

or the tautomeric form thereof

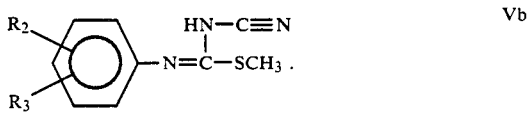

Reaction of compound Va or Vb with a compound of the formula

in a solvent, such as isopropanol, provides the compounds of formula I.

An alternative method for making compounds of formula I involves treating a compound of the formula

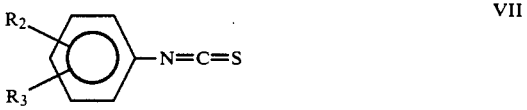

in the same manner as compound II above to provide a compound of the formula

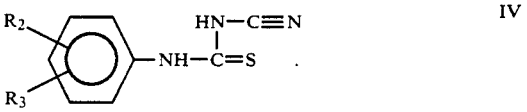

Compounds of formula IV are then treated with an amine of the formula R$_1$NH$_2$ and 1-(3-dimethylaminopropyl)-3-ethylcarbodiimide hydrochloride in a polar solvent such as dimethylformamide to provide compounds of formula I.

Compounds of formula I wherein $R_2$ is

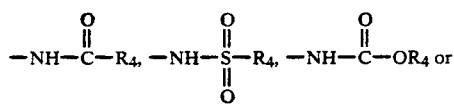

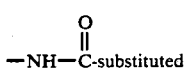

amino can be prepared from compounds of formula I where $R_2$ is a nitro group by first reducing the nitro group to an amino group to provide

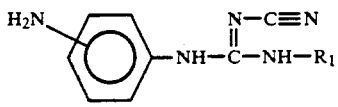  VIII by known techniques. Compound VIII is thereafter treated with an agent such as

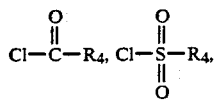

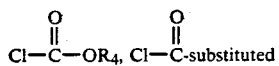

amino or $R_4N=C=O$ in an organic solvent and a base such as pyridine or triethylamine to provide the corresponding products of formula I.

If any of $R_1$, $R_2$, $R_3$, $R_4$ and $R_5$ in the above reactions are aryl or arylalkyl wherein aryl is phenyl substituted with one hydroxy or one or more amino groups, or a substituted alkyl such as hydroxylalkyl, aminoalkyl or mercaptoalkyl, then the hydroxyl, amino, or mercaptan function should be protected during the reaction. Suitable protecting groups include benzyloxycarbonyl, t-butoxycarbonyl, benzyl, benzhydryl, etc. The protecting group is removed by hydrogenation, treatment with acid, or by other known means following completion of the reaction.

Preferred compounds of this invention are those wherein:

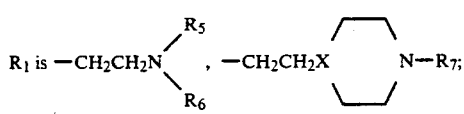

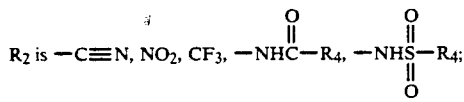

$R_3$ is hydrogen or alkyl; and

X is nitrogen or —CH—.

Most preferred compounds of this invention are those wherein:

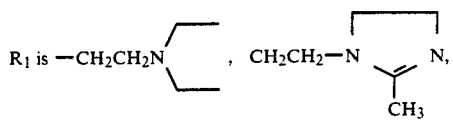

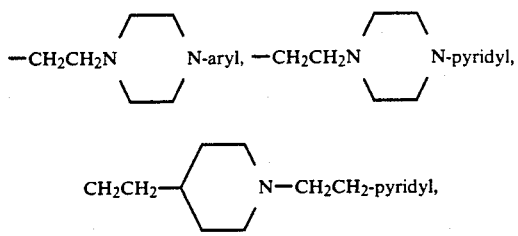

wherein pyridyl ring could be substituted with alkyl group;

$R_2$ is CN, $NO_2$,

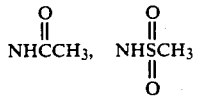

at the 4-position; and $R_3$ is hydrogen.

The compounds of formula I form salts with a variety of inorganic and organic acids. The non-toxic pharmaceutically acceptable salts are preferred, although other salts may also be useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

In addition, the compounds of formula I in which $R_2$-$R_4$ is

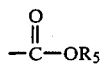

include carboxylic acid salts, i.e., $R_5$ is a pharmaceutically acceptable salt forming ion. Preferred salt forming ions include alkali metal salt ions such as sodium, potassium, and lithium, and alkaline earth metal salt ions such as calcium and magnesium.

The compounds of formula I and the pharmaceutically acceptable salts thereof are useful as cardiovascular agents. These compounds act as potassium channel blockers and are useful as antiarrhythmic agents.

The compounds of the present invention belong to class III antiarrhythmic agents (for classification of antiarrhythmic drugs see S. Donoghue and G. Allen, *Drugs of Today*, Vol. 24, No. 1, 1988, p. 39-52). The primary action of class III antiarrhythmic agents is to prolong the duration of the cardiac action potential and thereby increase effective refractory period in cardiac muscle. Class III agents slow the rate of ventricular tachycardia by lengthening the coupling interval of the premature response. They have very little or no effect on cardiac conduction and they increase QT interval on the electrocardiogram. These compounds are efficacious as antifibrillatory agents (atrial and ventricular fibrillation) in clinical as well as animal models of sudden cardiac death. They are useful to treat supraventricular tachycardias and ventricular tachyarrhythmias.

A single dose, or preferably two to four divided daily doses, provided on a basis of about 0.001 to 100 mg per kilogram of body weight per day, preferably from about 0.1 to about 25 mg per kilogram per day, is appropriate to reduce blood pressure. The substance is preferably administered orally, but parenteral routes, such as the subcutaneous, intramuscular, or intravenous routes or any other convenient delivery system can also be employed.

As a result of the potassium channel blocking activity of the compounds of formula I, it is believed that such compounds in addition to being antiarrhythmic agents may also be useful as antifibrillatory agents.

The compounds of this invention can also be formulated in combination with a diuretic, an angiotensin converting enzyme (ACE) inhibitor or a vasodilator. Suitable diuretics include the thiazide diuretics such as hydrochlorothiazide and bendroflumethiazide, suitable ACE inhibitors include captopril and enalapril and suitable vasodilators include nitroglycerin and sodium nitroprusside.

The compounds of formula I can be formulated in compositions such as tablets, capsules or elixirs for oral administration, or in sterile solutions or suspensions for parenteral administration. About 0.02 to 500 mg of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The present invention will be further illustrated by the following examples but should not be limited to the details described therein.

EXAMPLE 1

N''-Cyano-N-[2-(2-diethylamino)ethyl]-N'-(4-nitrophenyl)guanidine

A. N-Cyano-N'-(4-nitrophenyl)thiourea

A suspension of 4-nitrophenyl isothiocyanate (10.0 g, 55.5 mmol) and monosodium cyanamide (3.55 g, 55.5 mmol) in absolute ethanol (30 ml) was heated at 90° C. (oil bath) for 3.0 hours under argon. The reaction was then cooled (ice bath) and filtered to give a yellow solid (7.4 g), m.p. <230° C. TLC (10% MeOH/CH$_2$Cl$_2$) single spot, R$_f$=0.08.

B.   N''-Cyano-N-[2-(2-diethylamino)ethyl]-N'-(4-nitrophenyl)guanidine

A solution of the title A compound (3.3 g, 15.0 mmol) and 2-diethylaminoethyl amine (2.0 g, 18.0 mmol) in dimethylformamide (10 ml) under argon was treated with 1-(3-dimethylaminopropyl)-2-ethylcarbodiimide hydrochloride (3.8 g, 4.3 mmol). The reaction was stirred at room temperature for 1 hour and partitioned between aqueous sodium carbonate solution (pH~9) and ethyl acetate. The aqueous phase was reextracted with ethyl acetate and the combined organic layer was washed with water, sodium bicarbonate and brine. After drying over anhydrous magnesium sulfate, the solvent was evaporated and the residue was crystallized from ethyl acetate to provide the title compound (2.55 g, 55.9%), m.p. 154°–156° C.

$^1$H NMR (DMSO-d$_6$) δ8.2 (d, J=10.0 Hz, 2 H), 7.8 (br s, 1 H), 7.5 (d, J=10.0 Hz, 2 H), 3.4 (m, 2 H), 2.6 (m, 6 H), 1.0 (t, J=7 Hz, 6 H);

$^{13}$C NMR (DMSO) δ158.6, 145.3, 142.0, 124.8, 120.5, 116.5, 52.7, 46.7, 41.1, 11.1;

IR (KBr) 2170, 1518, 1490, 1268, 1126 cm$^{-1}$.

Analysis calc'd for C$_{14}$H$_{20}$N$_6$O$_2$: C, 55.24; H, 6.62; N, 27.62; Found: C, 55.24; H, 6.64; N, 27.24.

EXAMPLES 2–20

Using the methodologies described above, the following additional compounds within the scope of the present invention can be prepared.

EXAMPLE 2

N''-Cyano-N-[2-(diethylamino)ethyl]-N'-[4-[(methylsulfonyl)amino]phenyl]guanidine.

EXAMPLE 3

N-[4-(Acetylamino)phenyl-N''-cyano-N'-[2-(diethylamino)ethyl]guanidine.

EXAMPLE 4

N''-Cyano-N-(4-cyanophenyl)-N'-[2-(diethylamino)ethylguanidine.

EXAMPLE 5

N-(3-Chloro-4-nitrophenyl)-N''-cyano-N'-[2-(1piperidinyl)ethyl]guanidine.

EXAMPLE 6

N''-Cyano-N-(4-nitrophenyl)-N'-[2-4-(4-pyridinyl)-1-piperazinyl]ethyl]guanidine.

EXAMPLE 7

N''-Cyano-N-[2-[4-[2-(6-methyl-2-pyridinyl)ethyl]-1-piperazinyl]ethyl]-N'-[4-[(methylsulfonyl)amino]-phenyl]guanidine.

EXAMPLE 8

N-[4-(Acetylamino)phenyl]-N''-cyano-N'-[2-(4,5-dihydro-2-methyl-1H-imidazol-1-yl)ethyl ]guanidine.

EXAMPLE 9

N-(4-Acetylphenyl)-N''-cyano-N'-[2-(tetrahydro-4H-1,4-thiazin-4-yl)ethylguanidine.

EXAMPLE 10

N''-Cyano-N-[2-[4-(diphenylmethyl)-1-piperazinyl]-ethyl]-N'-[4-[(ethylsulfonyl)amino]phenyl]guanidine.

EXAMPLE 11

N-(4-Acetylphenyl)-N''-cyano-N'-[2-[1-[2-(6-methyl-2-pyridinyl)ethyl]-4-piperidinyl]ethyl]guanidine.

EXAMPLE 12

N''-Cyano-N-[2-(diethylamino)-1-methylethyl-N'-(3-methoxy-4-nitrophenyl)guanidine.

EXAMPLE 13

N''-Cyano-N-[2-(4-methyl-1-piperazinyl)ethyl]-N'-[4-[(1-pyrrolidinylcarbonyl)amino]phenyl]guanidine.

EXAMPLE 14

N''-Cyano-N-[2-(diethylamino)ethyl]-N'-[4-(methylsulfonyl)phenyl]guanidine.

EXAMPLE 15

N''-Cyano-N-[2-(4,5-dihydro-2-methyl-1H-imidazol-1-yl)ethyl]-N'-[4-[(methylsulfonyl) amino]phenyl]-guanidine.

EXAMPLE 16

N''-Cyano-N-[2-[methyl(phenylmethyl)amino]ethyl]-N'-[4-[(methylsulfonyl)amino]phenyl]guanidine.

EXAMPLE 17

N''-Cyano-N-[2-(diethylamino)ethyl]-N'-[4-(trifluoromethyl)phenyl]guanidine.

EXAMPLE 18

N''-Cyano-N-[4-[[(1-methylethoxy)carbonyl]amino]phenyl-N'-[2-[4-(phenylmethyl)-1-piperazinyl]ethyl]-guanidine.

EXAMPLE 19

N''-Cyano-N-[2-(diethylamino)ethyl-N'-(3-methoxy-4-nitrophenyl)guanidine.

EXAMPLE 20

N''-Cyano-N-(4-cyanophenyl)-N'-[2-(hexahydro-1H-azepin-1-yl)ethyl]guanidine.

What is claimed is:

1. Compounds having the formula

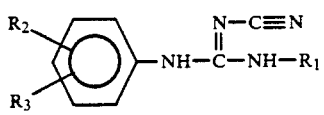

its possible tautomers

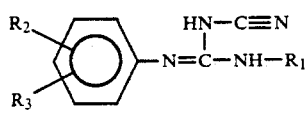

and

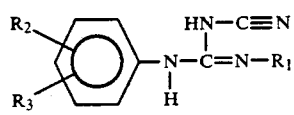

or a pharmaceutically acceptable salt thereof wherein $R_1$ is

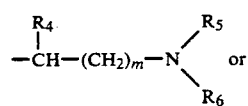

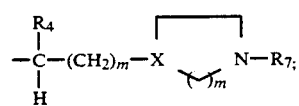

$R_2$ is hydrogen, alkyl, halo, —C|N,

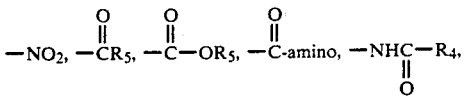

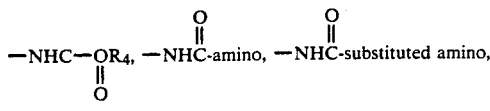

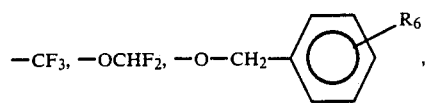

$R_3$ is hydrogen, alkyl, alkenyl, alkynyl, haloalkyl, halo, alkoxy, —NHalkyl, —N—(alkyl)$_2$, —S—alkyl, —O—arylalkyl or —S—arylalkyl;

$R_4$ is hydrogen, alkyl, alkenyl, cycloalkyl, haloalkyl, aryl, arylalkyl, cycloalkylalkyl;

$R_5$ and $R_6$ are each independently $R_4$ or together make a 5-7 membered ring consisting essentially of pyrrolidine, piperidene, morpholine, thiomorpholine, imidazoline, 2-alkylimidazoline, 1-azepinyl, with the proviso that if $R_5$ and $R_6$ are each hydrogen, one of $R_2$ and $R_3$ must be other than chloro;

$R_7$ is $R_4$, diphenylalkyl, pyridyl, pyridylalkyl wherein the pyridyl ring could be substituted with alkyl, arylalkyl, halo, haloalkyl;

$m = 1$ or 2; and

X is nitrogen or —CH— wherein the term alkyl refers to straight or branched chain saturated hydrocarbon radicals of one to eight carbons; the terms lower alkoxy and lower alkylthio refer to said alkyl groups attached to an oxygen or sulfur; the term lower alkenyl refers to straight or branched chain hydrocarbon radicals having from two to eight carbons and one double bond; the term lower alkynyl refers to straight or branched chain hydrocarbon radicals having from two to eight carbons and one triple bond; the term cycloalkyl refers to saturated carbocyclic rings of 4 to 7 carbon atoms; the term halo refers to chloro, bromo and fluoro;

the term halo substituted alkyl refers to such alkyl groups described above in which one or more hydrogens have been replaced by chloro, bromo or fluoro groups;

the term aryl refers to phenyl or mono substituted phenyl, wherein said substituent is lower alkyl of 1 to 4 carbons, lower alkylthio of 1 to 4 carbons, lower alkoxy of 1 to 4 carbons, halo, nitro, cyano, hydroxy, amino, -NH-lower alkyl wherein alkyl is of 1 to 4 carbons, -N(lower alkyl)$_2$ wherein alkyl is of 1 to 4 carbons,

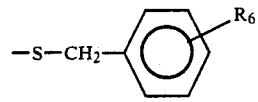

wherein $R_6$ is hydrogen, lower alkyl of 1 to 4 carbons, lower alkoxy of 1 to 4 carbons, lower alkylthio of 1 to 4 carbons, halo, hydroxy or $CF_3$), —O—$CH_2$-cycloalkyl, or —S—$CH_2$-cycloalkyl, and di-substituted phenyl, wherein said substituents are selected from methyl, methoxy, methylthio, halo, $CF_3$, nitro, amino, and $OCHF_2$; and the term "substituted amino" refers to a group of the formula —$NZ_1Z_2$ wherein $Z_1$ is hydrogen, alkyl, cycloalkyl, aryl, arylalkyl, cycloalkylalkyl and $Z_2$ is alkyl, cycloalkyl, aryl, arylalkyl, cycloalkylalkyl or $Z_1$ and $Z_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl substituted with alkyl, alkoxy, alkylthio, halo, trifluoromethyl or hydroxy.

2. A compound of claim 1 wherein

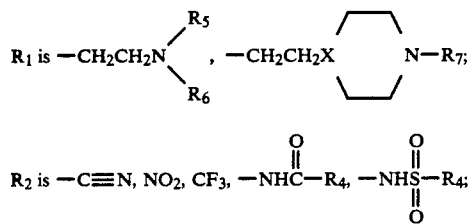

$R_3$ is hydrogen or alkyl; and
X is nitrogen or —CH—.

3. A compound of claim 1 wherein $R_1$ is

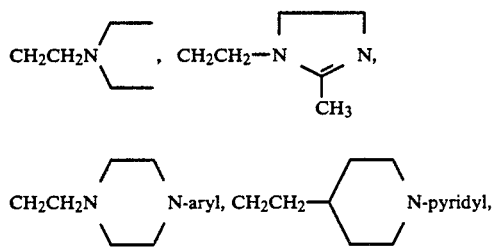

wherein pyridyl ring could be substituted with alkyl group;
$R_2$ is $NO_2$

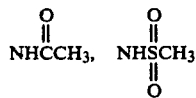

at the 4-position; and
$R_3$ is hydrogen.

4. A compound in accordance with claim 1 having the name N''-cyano-N-[2-(2-diethylamino)ethyl]-N'-(4-nitrophenyl)guanidine.

5. A compound in accordance with claim 1 having the name N''-cyano-N-[2-(diethylamino)ethyl]-N'-[4-[(methylsulfonyl)amino]phenyl]guanidine.

6. A compound in accordance with claim 1 having the name N-[4-(acetylamino)phenyl]-N''-cyano-N'-[2-(diethylamino)ethyl]guanidine.

7. A compound in accordance with claim 1 having the name N''-cyano-N-(4-cyanophenyl)-N'-[2-(diethylamino)ethyl]guanidine.

8. A compound in accordance with claim 1 having the name N-(3-chloro-4-nitrophenyl)-N''-cyano-N'-[2-(1-piperidinyl)ethyl]guanidine.

9. A compound in accordance with claim 1 having the name N''-cyano-N-(4-nitrophenyl)-N'-[2-[4-(4-pyridinyl)-1-piperazinyl]ethyl]guanidine.

10. A compound in accordance with claim 1 having the name N''-cyano-N-[2-[4-[2-(6-methyl-2-pyridinyl)ethyl-1-piperazinyl]ethyl]-N'-[4-[(methylsulfonyl)amino]phenyl]guanidine.

11. A compound in accordance with claim 1 having the name N-[4-(acetylamino)phenyl-N''-cyano-N'-[2-(4,5-dihydro-2-methyl-1H-imidazol-1-yl)ethyl]guanidine.

12. A compound in accordance with claim 1 having the name N-(4-acetylphenyl)-N''-cyano-N'-[2-(tetrahydro-4H-1,4-thiazin-4-yl)ethyl]guanidine.

13. A compound in accordance with claim 1 having the name N''-cyano-N-[2-[4-(diphenylmethyl)-1-piperazinyl]ethyl]-N'-[4-[(ethylsulfonyl)amino]phenyl]guanidine.

14. A compound in accordance with claim 1 having the name N-(4-acetylphenyl)-N''-cyano-N'-[2-[1-[2-(6-methyl-2-pyridinyl)ethyl-4-piperidinyl]ethyl]guanidine.

15. A compound in accordance with claim 1 having the name N''-cyano-N-[2-(diethylamino)-1-methylethyl]-N'-(3-methoxy-4-nitrophenyl)guanidine.

16. A compound in accordance with claim 1 having the name N''-cyano-N-[2-(4-methyl-1-piperazinyl)ethyl-N'-[4-[(1-pyrrolidinylcarbonyl)amino]phenyl]guanidine.

17. A compound in accordance with claim 1 having the name N''-cyano-N-[2-(diethylamino)ethyl]-N'-[4-(methylsulfonyl)phenyl]guanidine.

18. A compound in accordance with claim 1 having the name N''-cyano-N-[2-(4,5-dihydro-2-methyl-1H-imidazol-1-yl)ethyl]-N'-[4-[(methylsulfonyl)amino]phenyl]guanidine.

19. A compound in accordance with claim 1 having the name N''-cyano-N-[2-[methyl(phenylmethyl)amino]ethyl]-N'-[4-[(methylsulfonyl)amino]phenyl]guanidine.

20. A compound in accordance with claim 1 having the name N''-cyano-N-[2-(diethylamino)ethyl]-N'-[4-(trifluoromethyl)phenyl]guanidine.

21. A compound in accordance with claim 1 having the name N''-cyano-N-[4-[[(1-methylethoxy)carbonyl]amino]phenyl]-N'-[2-[4-(phenylmethyl)-1-piperazinyl]ethyl]guanidine.

22. A compound in accordance with claim 1 having the name N''-cyano-N-[2-(diethylamino)ethyl]-N'-(3-methoxy-4-nitrophenyl)guanidine.

23. A compound in accordance with claim 1 having the name N''-cyano-N-(4-cyanophenyl)-N'-[2-(hexahydro-1H-azepin-1-yl)ethyl]guanidine.

24. A pharmaceutical composition useful for the treatment of arrhythmic conditions in mammalian species which comprises a therapeutically effective amount of a compound of formula I in claim 1 and a pharmaceutically acceptable carrier therefor.

25. A method for the treatment of arrhythmia in mammalian species which comprises administering a therapeutically effective amount of a compound of formula I in claim 1 to a specie in need thereof.

26. A method for the treatment of atrial or ventricular fibrillation in a mammalian species which which comprises administering a therapeutically effective amount of a compound of formula I in claim 1 to a specie in need thereof.

27. A method for the treatment of supraventricular tachycardia and/or ventricular tachyarrhythmia in a mammalina species which comprises administering a therapeutically effective amount of a compound of formula I in claim 1 to a specie in need thereof.

* * * * *